United States Patent [19]
Riley, Jr.

[11] Patent Number: 5,266,329
[45] Date of Patent: Nov. 30, 1993

[54] VAGINAL DELIVERY SYSTEM

[75] Inventor: Thomas C. Riley, Jr., St. Louis, Mo.

[73] Assignee: KV Pharmaceutical Company, St. Louis, Mo.

[21] Appl. No.: 798,873

[22] PCT Filed: Oct. 31, 1985

[86] PCT No.: PCT/US85/02145

§ 371 Date: Jun. 12, 1987

§ 102(e) Date: Jun. 12, 1987

[87] PCT Pub. No.: WO87/02576

PCT Pub. Date: May 7, 1987

Related U.S. Application Data

[63] Continuation of Ser. No. 659,686, Feb. 25, 1991, abandoned, which is a continuation of Ser. No. 60,051, Jun. 12, 1987, abandoned.

[51] Int. Cl.$^5$ ............................................. A61F 6/06
[52] U.S. Cl. .................................. 424/430; 424/433; 424/450; 514/964; 514/965; 514/467
[58] Field of Search ............... 424/430, 434, 435, 433, 424/464; 514/964, 965, 967, 939, 966

[56] References Cited

U.S. PATENT DOCUMENTS

| | | | |
|---|---|---|---|
| 2,238,973 | 4/1941 | Climenko | 167/65 |
| 2,467,884 | 4/1949 | Elias | 167/58 |
| 2,469,618 | 5/1949 | Ward et al. | 167/64 |
| 2,541,103 | 2/1951 | Sander | 167/58 |
| 2,623,839 | 12/1951 | Taub | 167/58 |
| 3,144,386 | 8/1956 | Brightenback | 167/53 |
| 3,219,525 | 11/1965 | Berkow | 167/58 |
| 3,238,103 | 3/1966 | Vogenthaler | 167/82 |
| 3,244,589 | 4/1966 | Sunnen et al. | 167/58 |
| 3,339,546 | 9/1967 | Chen | 128/156 |
| 3,384,541 | 5/1968 | Clark | 167/58 |
| 3,751,562 | 8/1973 | Nichols | 424/45 |
| 3,921,636 | 10/1975 | Zaffaroni | 128/260 |
| 3,946,106 | 3/1976 | Chien et al. | 424/424 |
| 4,351,948 | 9/1982 | Fellner et al. | 548/336 |
| 4,356,167 | 10/1982 | Kelly | 424/38 |
| 4,385,049 | 5/1983 | Cuea | 514/939 |
| 4,396,630 | 8/1983 | Riedl et al. | 424/365 |
| 4,427,649 | 12/1984 | Dingle et al. | 424/38 |
| 4,542,020 | 9/1985 | Jackson et al. | 514/31 |
| 4,551,148 | 11/1985 | Riley, Jr. et al. | 424/430 |
| 4,803,066 | 2/1989 | Edwards | 424/464 |
| 5,055,303 | 10/1991 | Riley, Jr. | 514/966 |

FOREIGN PATENT DOCUMENTS 2004462  9/1978  United Kingdom .
2139919  11/1984  United Kingdom .

Primary Examiner—Thurman K. Page
Assistant Examiner—Jyothsna Venkat
Attorney, Agent, or Firm—Nath, Lambert & Amberly

[57] ABSTRACT

Systems and their methods of preparation and use that release an active agent in a controlled manner for an extended period in a vaginal cavity environment. When an antifungal agent such as an imidazole, is incorporated into the system it has been found that the conventional treatment time is reduced by at least 25%.

7 Claims, No Drawings

VAGINAL DELIVERY SYSTEM

This application is a continuation of application Ser. No. 07/659,686 filed Feb. 25, 1991, now abandoned, which is a continuation of application Ser. No. 07/060,051 filed Jun. 12, 1987, also abandoned.

BACKGROUND OF THE INVENTION

1. Field of the Invention

The present invention is directed to delivery systems which are suitable for use in the vaginal cavity. Specifically, the invention is concerned with vaginal preparations which demonstrate the controlled-release of active agents for an extended period of time to a site of action or absorption.

2. Description of the Prior Art

One of the main disciplines of medicine is the treatment of the female reproductive system for the prevention, treatment, mitigation, diagnosis and cure of diseases and the prevention of conception. Usually, this involves the delivery of active agents to the vaginal cavity and its environs. Systems to effect the delivery of such agents are usually in the form of gels, foams, creams, suppositories and quick dissolving tablets. These delivery systems, regardless of formulation or method of manufacture, have not demonstrated the ability to deliver active agents in a controlled manner within the vaginal cavity for periods of three hours or longer.

The vaginal cavity is subject to conditions which render it a target for disease and infection; however, it is extremely difficult to deliver an active agent to this area for an extended period of time. The vaginal cavity exhibits an aqueous environment containing secreting glands whose fluids create an acidic pH in the range of 4.5 to 5.5. The environment of the vagina is conducive to the growth of bacteria, fungi, yeast and other microorganisms since it is warm, moist and dark. It is also the vestibule for menstrual debris and the residual seminal fluid from sexual intercourse. The crevices of the vaginal cavity facilitate the retention of undesirable bacteria, fungi, yeast and other microorganisms, as well as the debris from menstruation and sexual intercourse. The vaginal cavity is also subject to considerable physical deformation, such as during sexual intercourse or during the insertion of tampons.

Active agents which have pharmaceutical qualities have been developed and approved for use in the treatment of afflictions of the vaginal cavity and the prevention of conception. These include fungicides, spermicides, etc. Although pharmaceutically active agents have been developed, it has been difficult to achieve optimal potential effectiveness from these agents due to the inadequacy of currently available delivery systems. No system which is approved or even suitable for use in the vaginal cavity has been shown to release a pharmaceutically active agent for periods of three hours or longer. This also is true of aesthetically oriented systems, such as acidifiers and deodorants. The gels, foams, creams, suppositories and tablets that are presently used as vaginal delivery systems breakdown almost immediately following insertion into the vaginal cavity and have minimal bioadherence to the vaginal walls. This is believed to be due to their water miscability and/or their lack of physical stability at 37 degrees C. (body temperature). Thus, they exhibit limited effectiveness since they rapidly release their active agents in an uncontrolled manner. Conventional dosage forms are frequently discharged as an offensive leakage and drippage along with the minute vaginal secretions that are a normal physiological function.

A controlled release system delivers the active agent to the sits of action, absorption or use in a predetermined manner. This contrasts with conventional immediate release systems which require frequent repetitive dosing in order to achieve the desired level of active agent. An advantage of a controlled release system is that the drug is administered fewer times a day than conventional systems since the drug level in the vaginal cavity is maintained at a constant level. The controlled release systems of the prior art do not affect the total number of days that are required to treat a condition.

The present invention is advantageous in that it provides a system for the delivery of an active agent in a controlled manner in the vaginal cavity for an extended period of at least three hours. The system may take the form of a multi-phase liquid or semi-solid which is easily introduced into the vaginal cavity but does not seep from this body cavity in an offensive manner. It is further advantageous since it reduces the treatment period for active agents including antifungals, such as, imidazoles.

SUMMARY OF THE INVENTION

The invention provides vaginal delivery systems which release an active agent to a site of absorption or action in a controlled manner and are bioadherent to the vaginal surfaces. The invention also provides vaginal delivery systems which release an active agent to a site of absorption or action in a controlled manner for at least three hours and are bioadherent to the vaginal surfaces comprising unit cells having lipoidal external phases and nonlipoidal internal phases.

DESCRIPTION OF THE PREFERRED EMBODIMENTS

The present invention is directed to vaginal delivery systems. The systems are characterized by their ability to deliver agents to a specific site, the vaginal cavity, in a controlled manner over a prolonged period of time. The systems are bioadherent to the epithelial tissue and are comprised of at least two phases. The systems when in a vaginal environment retain their integrity and display physical stability for an extended residence time within the vaginal cavity.

As discussed above, the vaginal cavity produces an aqueous environment which is conducive to the growth of bacteria, fungi, yeast and microorganisms. The systems of the prior art are not optimally effective for treating such conditions either due to their water miscability, lack of bioadhesion, or lack of physical stability in the vaginal environment of 37 degrees C. The vaginal cavity as defined herein not only includes the vagina, but also associated surfaces of the female urinary tract, such as, the ostium of the urethra. Delivery systems are a combination of nonactive ingredients which serve to solubilize, suspend, thicken, dilute, emulsify, stabilize, preserve, protect, color, flavor and fashion an active agent into an acceptable and efficacious preparation for the safe and convenient delivery of an accurate dose of said active agent.

It is important that a system not only release an active agent, but that it release the agent in a controlled manner to a site of optimal absorption or action. That is, an agent is made available for absorption, pharmacological or other effect at a site of absorption or action, in an amount sufficient to cause a desired response consistent with the intrinsic properties of the agent and which provides for maintenance of this response at an appropriate level for a desired period of time. Thus, the systems described herein are characterized by the controlled release of an active substance from a delivery system at a receptor site, site of action, site of absorption, or site of use and the achievement of the desired effect at that site. The systems of the invention are not miscible in water and are not harmful for use in the vaginal cavity.

The systems are comprised of unit cells. These unit cells are the basic, nondivisible, repeating unit of the systems. The unit cells have internal and external phases which represent the internal and external phases of the systems. The systems may be described in conventional classifications, such as emulsions, emulsions/dispersion, double emulsions, suspensions within emulsions, suppositories, foams, etc. The systems are usually in the form of emulsions either of medium or high internal phase ratio, preferably greater than 70% and more preferably greater than 75% by volume. The delivery systems are liquids or semi-solids with viscosities that range from 5,000 to 750,000 centipoise, preferably 350,000 to 550,000 centipoise. The systems in order to adhere to the vaginal cavity must have sufficient viscosity to retain their integrity.

The unit cells have an internal phase which may be discontinuous and which is nonlipoidal. The nonlipoidal character of the phase renders it miscible with water. Preferably the internal phase comprises water, glycerine, or combinations thereof. Generally, it is desirable that the internal phase be of high osmotic pressure. The internal phase may be multiphasic and may be a solution, suspension, emulsion or combination thereof and it contains at least a portion of the active agent. Also, the internal phase may contain suspended solids, emulsions, osmotic enhancers, extenders and dilutants, as well as fragrances, colors, flavors, and buffers.

The unit cells also have an external phase. This phase is lipoidal and is the continuous phase of the systems. The term lipoidal pertains to any of a group of organic compounds comprising the neutral fats, fatty acids, waxes, phosphatides, petrolatum, fatty acid esters of monoprotic alcohols and mineral oils having the following common properties: insoluble in water, soluble in alcohol, ether, chloroform or other fat solvents, and which exhibit a greasy feel. Examples of oils suitable for use in these delivery systems are mineral oils with viscosities of 5.6 to 68.7 centistokes, preferably 25 to 65 centistokes, and vegetable oils illustrated by coconut, palm kernel, cocoa butter, cottonseed, peanut, olive, palm, sunflower seed, sesame, corn, safflower, rape seed, soybean and fractionated liquid triglycerides of short chain (naturally derived) fatty acids. This external phase may also contain fragrances, colors, flavors, and buffers.

The active agent may be any of those which are approved for or used for the treatment, prophylaxis, cure or mitigation of any disease of the vagina, urinary tract, cervix or other female reproductive organ or inducement of conception; for aesthetic or cosmetic usage, for diagnostic purposes; for systemic drug therapy; or for sex determination of offspring. The agent must have utility when administered by delivery to all or a portion of the vaginal surfaces. Potential agents are normally well-known due to their need for governmental approval or common usage. At least a portion of the active agent must usually be contained in the internal phase in order to obtain the release characteristics of the systems.

It has been found that when active agents including antifungals, such as, imidazoles, are used as part of the active agent, the conventional treatment period or quantity of agent used is reduced by at least 25%. Normally a controlled release drug system reduces the number of times a day that a drug must be administered. However, it does not affect the overall length of treatment. With respect to certain active agents it has been discovered that the drug delivery system described herein reduces the treatment period by at least 25%. Tests utilizing imidazoles upon Candida albicans have demonstrated this unexpected result. It is believed that this effect can be achieved with other antibacterial agents and antifungal agents. Thus, the treatment of microbes can be achieved in much shorter time or with substantially less drug with the system of the invention.

Adjacent unit cells have common external phases. The external phase of the unit cells provides the continuous phase of the system. The unit cells may utilize emulsifiers. Preferably, the emulsifiers are soluble in the lipoidal or external phase. Suitable emulsifiers are those oil miscable surface active compounds which are acceptable for use in foods, pharmaceuticals, and/or cosmetics. Examples of such emulsifiers are low molecular weight polyglycerols which have been esterified with fatty acids or fatty acid esters, or mono and diglyceride mixtures alone or with the addition of metallic soaps, such as, aluminum stearate. The metallic soaps appear to improve the characteristics of some of the emulsions.

The systems can be introduced into the vaginal cavity by the use of conventional applicators or other coating or spraying means. Although the systems are deformable at physiological temperatures, approximately 37 degrees C., they do not lose their integrity as do the systems of the prior art. These delivery systems, unlike other systems, are not characterized by offensive leakage from the vaginal cavity following the insertion of the system. Since these systems break down over an extended period, nonaqueous components are either absorbed or released from the vaginal cavity at an unnoticeable rate which makes no significant increase in normal secretions.

The characteristics of these systems are a result of their inherent integrity under vaginal conditions. The systems release the active agent in the vaginal cavity due to diffusion of the active agent, rupture of the unit cells and/or a combination of these two mechanisms. This release of active agent can be linear or non-linear depending on the composition of the system. Factors which effect the release rate are the percentage of active agent contained in each of the phases; and the type of system, such as, emulsion, double emulsion, suspension; thickness of the external membrane; amount and nature of emulsifier in the external phase; osmotic pressure of the internal phase; pH of the internal phase; diffusibility of the active species through the external phase membrane; etc. Within the physiological environment of the vaginal cavity all of the chemical and physical forces present, including fluids, enzymes, pH, chemical balance, temperature, and shear forces from body movement, affect the rate of breakdown of the system. These forces do not destroy the integrity of the systems at the same rate as other systems.

The systems may be prepared by continuous or batch processes. As in preparing conventional emulsions, shear force is applied to the system components by use of homogenizers, mills, impingement surfaces, ultrasound, shaking or vibration. Unlike conventional emulsions, the mixing shear should be at low levels in order to prevent destruction of the system by imparting excess energy. Temperature is not usually a critical factor in the preparation of the systems. The temperatures utilized will be dependent upon the final end product desired.

The systems may be prepared by mixing the internal with the external phase in a planetary-type mixer. Another manner of preparing the system is by use of a continuous mixer which comprises multiple impellers. The external phase is first introduced into the continuous mixer until it reaches the level of the lowest impeller in the mixing chamber. The two phases are then simultaneously introduced through the bottom of the mixer in proper proportion as its impeller or impellers rotate to apply a shear to the components. The finished product emerges through the top of the mixer. The actual speed of the impeller or impellers will vary, depending upon the product produced as will the rate of flow of the two phase streams.

The following examples are illustrative of the invention:

Method of Preparation: The active agent and ingredients of the internal phase were mixed together at room temperature. The ingredients of the external phase were mixed together in a one-gallon vessel. The internal phase composition was slowly added to the external phase composition as the two phases were mixed together with a split disc stirrer at low shear until the desired viscosity was obtained.

The same products were also prepared by introducing the internal and external phases continuously into the bottom of a mixer following the initial introduction of the external phase. The finished product emerged through the top of the mixer at one liter/minute.

| Ingredients | % wt./wt. |
|---|---|
| SPERMICIDE Viscosity = 168M centipoise | |
| Internal Phase | |
| Nonoxynol-9 | 2.83 |
| Deionized Water | 42.22 |
| Sucrose | 15.32 |
| Sorbitol | 15.75 |
| Glycerine | 8.73 |
| Agar | 1.13 |
| Starch | 1.13 |
| Citric Acid | 1.42 |
| External Phase | |
| Mineral Oil | 7.37 |
| Polyglycerol Ester | 3.90 |
| Methylparaben | 0.13 |
| Propylparaben | 0.07 |
| | 100.00 |
| NYSTATIN Viscosity = 400M centipoise | |
| Internal Phase | |
| Nystatin | 2.16 |
| Sucrose | 30.26 |
| Deionized Water | 60.43 |
| External Phase | |
| Mineral Oil | 5.48 |
| Polyglycerol Ester | 1.50 |
| Methylparaben | 0.13 |
| Propylparaben | 0.04 |
| | 100.00 |

| Ingredients | % wt./wt. |
|---|---|
| VAGINAL BUFFER Viscosity = 424M centipoise | |
| Internal Phase | |
| Citric Acid | 4.04 |
| Sodium Citrate | 1.22 |
| Deionized Water | 44.77 |
| Sucrose | 16.25 |
| Sorbitol | 16.70 |
| Glycerine | 9.25 |
| External Phase | |
| Mineral Oil | 5.91 |
| Polyglycerol Ester | 1.66 |
| Methylparaben | 0.13 |
| Propylparaben | 0.07 |
| | 100.00 |
| ANTIFUNGAL | |
| Internal Phase | |
| deionized water | 42.895 |
| sorbitol solution | 39.978 |
| metronidazole | 2.00 |
| disodium EDTA | 0.05 |
| External Phase | |
| dimethicone | 4.016 |
| mineral oil | 4.016 |
| glyceryl isostearate | 2.713 |
| polyglyceryl-4 oleate | 2.713 |
| colloidal silicon dioxide | 1.013 |
| microcrystalline wax | .452 |
| methyl paraben | .127 |
| propyl paraben | .027 |
| | 100.00 |

Each of the above compositions following introduction into the vaginal cavity continued to release its active agent at effective levels for a period of between three hours and ten days. Systems of the prior art containing the same active agent had completely released their active agent within a three hour period.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

We claim:

1. Vaginal delivery systems adapted for the treatment of fungal infections, which are bioadherent to the surfaces of a vaginal cavity comprising an active antimicrobial agent comprising an imidazole adapted to be released in a controlled manner to a location selected from the group consisting of a receptor site, site of action, site of absorption or site of use wherein said vaginal delivery systems comprise at least two phases, one phase comprises an external lipoidal phase and the other phase comprises an internal nonlipoidal phase wherein said lipoidal phases is continuous and the said nonlipoidal phases comprises at least 70% by volume of said systems, which vaginal delivery systems allow the overall treatment period or quantity of imidazole utilized to treat said fungal infection to be reduced by at least 25%.

2. The vaginal delivery systems of claim 1, wherein said phases form to comprise an emulsion, emulsion/dispersion, double emulsion, suspension within an emulsion or mixture.

3. A vaginal delivery drug system which comprise at least two phases, one phase comprises an external lipoidal phase and the other phase comprises an internal nonlipoidal phase wherein said lipoidal phases is continuous and the said nonlipoidal phases comprises at least 70% by volume of said system, which vaginal delivery system are for the treatment of microorganisms, wherein said vaginal drug delivery system is in a form selected from a liquid or semi-solid comprising a high internal phase ratio emulsion having an active antimicrobial agent present in an amount effective to reduce overall treatment period or quantity of active antimicrobial agent utilized by at least 25%.

4. A method of treating a vaginal fungal infection in a female human, which comprises: administering to the vaginal cavity of said human a therapeutically effective amount of a bioadherent, liquid or semi-solid vaginal delivery system comprising at least two phases, one phase comprises an external lipoidal phase and the other phase comprises an internal nonlipoidal phase wherein said lipoidal phases is continuous and the said nonlipoidal phases comprises at least 70% by volume of said systems, and which vaginal delivery system comprises a high internal phase ratio emulsion containing a therapeutically effective amount of an active antimicrobial agent comprising an antifungal agent, wherein the overall treatment period or quantity of antifungal agent utilized to treat said fungal infection is reduced by at least 25%.

5. The vaginal delivery systems of claim 1, wherein the active antimicrobial agent is an antifungal agent or an antibacterial agent.

6. The vaginal drug delivery system of claim 3, wherein the active antimicrobial agent is an antibacterial agent or an antifungal agent.

7. The method of treating a vaginal fungal infection of claim 4, wherein the active antimicrobial agent is an imidazole agent.

* * * * *